Figure 1:
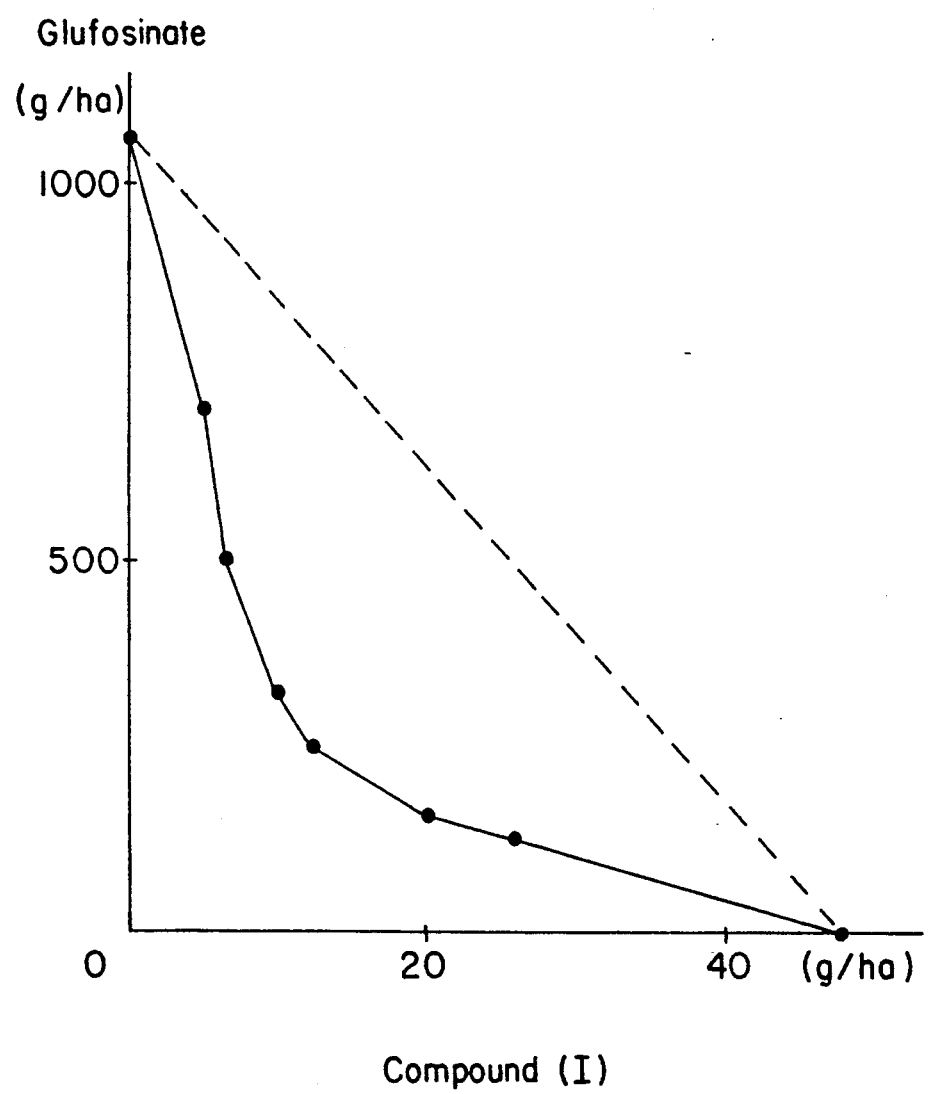

United States Patent [19]

Yoshida et al.

[11] Patent Number: 5,173,103
[45] Date of Patent: Dec. 22, 1992

[54] HERBICIDAL COMPOSITION COMPRISING 2-[7-FLUORO-3,4-DIHYDRO-3-OXO-4-(2-PYROPYNYL)-2H-1,4-BENZOXAZIN-6-YL]-4,5,6,7-TETRAHYDRO-1H-ISOINDOLE-1,3(2H)-DIONE AND EITHER GLUFOSINATE OR BIALAPHOS

[75] Inventors: Ryo Yoshida, Misawa; Yoshihiro Mano, Toyonaka; Hideyuki Shibata, Takarazuka, all of Japan

[73] Assignee: Sumitomo Chemical Co., Ltd., Osaka, Japan

[21] Appl. No.: 841,277

[22] Filed: Feb. 26, 1992

Related U.S. Application Data

[63] Continuation of Ser. No. 373,456, Jun. 30, 1989, abandoned.

[30] Foreign Application Priority Data

Jul. 5, 1988 [JP] Japan .................... 63-167925

[51] Int. Cl.⁵ .................... A01N 43/38; A01N 43/84; A01N 57/10
[52] U.S. Cl. .................... 71/86; 71/96; 71/DIG. 1
[58] Field of Search .................... 71/86, 96

[56] References Cited

U.S. PATENT DOCUMENTS

| | | | |
|---|---|---|---|
| 4,168,963 | 9/1979 | Rupp et al. | 71/86 |
| 4,309,208 | 1/1982 | Takematsu et al. | 71/86 |
| 4,640,707 | 2/1987 | Nagano et al. | 71/96 |
| 4,692,181 | 9/1987 | Bieringer et al. | 71/86 |

OTHER PUBLICATIONS

"General survey on Herbicide" by Hakuyusha, pp. 611–612, 1982.

"The Pesticide Manual" Published by the British Crop Protection Council, Eight Edition, 1987, p. 6930.

*Primary Examiner*—Richard L. Raymond
*Assistant Examiner*—Brian G. Bembenick
*Attorney, Agent, or Firm*—Birch, Stewart, Kolasch & Birch

[57] ABSTRACT

A herbicidal composition which comprises a herbicidally effective amount of the combinations of (a) 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione and (b) at least one of (2-amino-4-methylphosphinobutyryl)alanylalanine and its salt (bialaphos) and DL-homoalanin-4-yl(methyl)phosphinic acid and its salt (glufosinate), and an inert carrier or diluent. The composition exerts synergistic herbicidal activity.

18 Claims, 3 Drawing Sheets

HERBICIDAL COMPOSITION COMPRISING 2-[7-FLUORO-3,4-DIHYDRO-3-OXO-4-(2-PYROPYNYL)-2H-1,4-BENZOXAZIN-6-YL]-4,5,6,7-TETRAHYDRO-1H-ISOINDOLE-1,3(2H)-DIONE AND EITHER GLUFOSINATE OR BIALAPHOS

This application is a continuation of Ser. No. 07/373,456 filed on Jun. 30, 1989, now abandoned.

The present invention relates to a herbicidal composition. More particularly, it relates to a herbicidal composition comprising as the active ingredients (a) 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione (hereinafter referred to as "Compound (I)") of the formula:

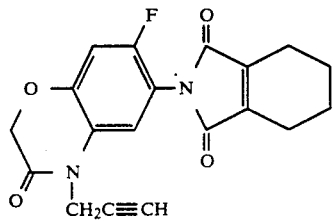

and (b) at least one of (2-amino-4-methylphosphinobutyryl)alanylalanine of the formula:

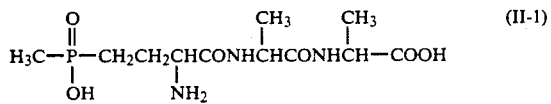

or its salt (hereinafter referred to as "bialaphos") and DL-homoalanin-4-yl(methyl)phosphinic acid of the formula:

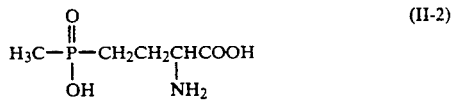

or its salt (hereinafter referred to as "glufosinate").

In recent years, there have been used a great number of chemicals having herbicidal activities in order to exterminate or control undesired vegetation of weeds used in agricultural and non-agricultural fields. Since, however, weeds are diversified in kinds and grow over a long period of time, the herbicidal effects of conventional herbicidal agents are restricted in general. Under the circumstances, the appearance of any herbicidal agent exerting a strong herbicidal activity as well as a broad herbicidal spectrum over a wide variety of weeds has been highly demanded. Besides, rainfall just after the herbicidal treatment frequently reduces the designated herbicidal effect as expected, and eventual retreatment becomes necessary. It is thus desirable that the herbicidal activity will not be reduced on rainfall.

As a result of an extensive study, it has now been found that the associated use of (a) Compound (I) with (b) at least one of bialaphos (II-1) and glufosinate (II-2), these being hereinafter referred to as "Compounds (II)", produces a highly enhanced herbicidal activity against a wide variety of weeds in agricultural and non-agricultural fields. In comparison with the sole use of each of said active ingredients, enhancement of the herbicidal potency with regard to such associated use is remarkable so that the active ingredients may be applied in smaller dosages. Further, the weed-control spectrum is greatly enlarged. Furthermore, reduction of the herbicidal potency due to rainfall may be suppressed by the associated use.

The herbicidal composition of the invention comprising Compound (I) and Compound(s) (II) can exterminate or control a variety of weeds, of which typical examples are broad-leaved weeds such as wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Pharbitis purpurea*), field bindweed (*Convolvulus arvensis*), purple deadnettle (*Lamium purpureum*), henbit (*Lamium amplexicaure*), jimsonweed (*Datura stramonium*), black nightshade (*Sllanum nigrum*), persian speedwell (*Veronica persica*), common cocklebur (*Xanthium strumarium*), common sunflower (*Helianthus annuus*), scentless chamomile (*Matricaria perforata*), corn marigold (*Chrysanthemum segetum*), curly dock (*Rumex crispus*) and Japanese mugwort (*Artemisia princeps*), stichwort water (*Myosoton aquaticum*), japanese hedgeparsley (*Torilis japonica*), tall goldenrod (*Solidago altissima*) and common vetch (*Vicia sativa*); graminaceous weeds such as bluestem colorado (*Agropyron tsukushiense*), japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*) and bermudagrass (*Cynodon dactylon*); commelinaceous weeds such as asiatic dayflower (*Commelina communis*); cyperaceous weeds such as rice flatsedge (*Cyperus iria*) and purple nutsedge (*Cyperus rotundus*), etc.

Compound (I) is known to exert herbicidal activity (U.S. Pat. No. 4,640,707). Bialaphos (II-1) is described in Tetsuo Takematsu: General Survey on Herbicide, page 611 (1982) and used as a herbicide in a free or an agriculturally acceptable salt form (e.g. sodium salt). Glufosinate (II-2) is also described in C. R. Worthing et al: The Pesticide Mannual, 8th Ed., page 448 (1987) and used as a herbicide in a free or an agriculturally acceptable salt form (e.g. ammonium salt). However, the associated use of Compound (I) with any of Compounds (II) has never been attempted, and the production of synergism as well as resistance to rain on the associated use has never been expected.

The proportion of Compound (I) as the component (a) and Compound(s) (II) as the component (b) in the composition of the invention may vary in a considerably broad range and is usually within a range of 1 : 0.5 to 1 : 100 by weight, particularly 1 : 1 to 1 : 70 by weight.

In addition to the above active ingredients, the composition may contain a solid or liquid carrier or diluent. Any surface active or auxiliary agent may be also contained therein. Thus, the composition may be formulated in any conventional preparation form such as wettable powder or suspension. The total content of the active ingredients, i.e. Compound (I) and Compound(s) (II), may be from 1 to 90 by weight, preferably from 2 to 80% by weight.

As the solid carrier or diluent, there may be used kaolin clay, attapulgite clay, bentonite, terra alba, pyrophyllite, talc, diatomaceous earth, calcite, wallnut-shell powder, urea, ammonium sulfate, synthetic hydrated silica, etc. Examples of the liquid carrier or diluent are water, etc.

The surface active agent used for dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the composition are illustratively shown in the following Formulation Examples wherein part(s) are by weight.

FORMULATION EXAMPLE 1

Five parts of Compound (I), 50 parts of bialaphos, 3 parts of calcium ligninsulfonate, 2 parts of sodium laurylsulfate and 40 parts of synthetic hydrated silica are mixed well and pulverized to obtain a wettable powder.

FORMULATION EXAMPLE 2

One part of Compound (I), 20 parts of glufosinate, 3 parts of polyoxyethylene sorbitan monooleate, 3 parts of CMC and 73 parts of water are mixed and pulverized until the particle size becomes less than 5 microns to make a suspension.

FORMULATION EXAMPLE 3

One part of Compound (I), 20 parts of bialaphos, 3 parts of polyoxyethylene sorbitan monooleate, 3 parts of CMC and 73 parts of water are mixed and pulverized until the particle size becomes less than 5 microns to make a suspension.

FORMULATION EXAMPLE 4

Five parts of Compound (I), 50 parts of glufosinate, 3 parts of calcium ligninsulfonate, 2 parts of sodium laurylsulfate and 40 parts of synthetic hydrated silica are mixed well and pulverized to obtain a wettable powder.

FORMULATION EXAMPLE 5

Forty parts of Compound (I), 40 parts of bialaphos, 3 parts of calcium ligninsulfonate, 2 parts of sodium laurylsulfate and 15 parts of synthetic hydrated silica are mixed well and pulverized to obtain a wettable powder

FORMULATION EXAMPLE 6

0.7 Part of Compound (I), 49 parts of glufosinate, 3 parts of calcium ligninsulfonate, 2 parts of sodium laurylsulfate and 45.3 parts of synthetic hydrated silica are mixed well and pulverized to obtain a wettable powder.

FORMULATION EXAMPLE 7

0.4 Part of Compound (I), 1.6 parts of bialaphos, 1 part of polyoxyethylene sorbitan monooleate, 1 part of CMC and 96 parts of water are mixed and pulverized until the particle size becomes less than 5 microns to make a suspension.

FORMULATION EXAMPLE 8

0.4 Part of Compound (I), 10 parts of "Sorpol 5050" ® (an anionic surface active agent manufactured by Toho Yakuhin Kogyo K.K.; containing 50% dialkylsulfosuccinate), 4 parts of sodium ligninsulfonate, 5 parts of synthetic hydrated silica, 79 parts of clay are mixed well. 1.6 Parts of glufosinate are added thereto, and the mixture is pulverized well to obtain a wettable powder.

A composition comprising Compound (I) and Compound(s) (II) thus formulated is useful for post-emergence control of undesired weeds by foliar treatment. The foliar treatment may be effected by spraying the composition containing Compound (I) and Compound(s) (II) over the top of plants. The direct application may also be adopted.

In order to improve the herbicidal activity, the composition may be used with other herbicides. Besides, it may be used in combination with insecticides, acaricides, nematocides, fungicides, plant growth regulators, fertilizers, soil improvers, etc.

The composition of the invention is widely used as the herbicide applicable in plowed field, non-cropping land, orchards, pasture land, lawn, forest, non-agricultural fields, etc.

The dosage of the active ingredients may vary depending on prevailing weather conditions, soil involved, formulation used, mixing proportion of each active ingredient, crop and weed species, etc. In general, however, the total amount of Compound (I) and Compound(s) (II) may be within a range of about 100 to 4000 grams per hectare, preferably within a range of about 150 to 2000 grams per hectare, more preferably within the range of about 200 to 2000 grams per hectare.

The composition in the form of wettable powder, suspension or the like is normally diluted with water and applied at a volume of 100 to 2000 liters per hectare to the area where extermination of weeds is desired. The dilution may further include, in addition to the above mentioned surface active agent, any spreading or auxiliary agent such as polyoxyethylene resin acid esters, ligninsulfonates, abietic acid, dinaphthylmethanedisulfonates, paraffin, petroleum oil and the like.

The herbicidal activity of the composition of the invention will be explained in further detail with reference to the following Test Examples. Further, throughout Test Examples, bialaphos and glufosinate are respectively used in the form of sodium salt and ammonium salt.

TEST EXAMPLE 1

Upland fields soil were filled in Wagner pots (inner diameter, 16 cm; height, 19 cm), and seeds of catchweed bedstraw, bluestem colorado and stichwort water were sowed therein and cultivated outdoors for 5 months. A designed amount of the composition in the form of a wettable powder formulated according to Formulation Example 1, 4, 5 or 6 was diluted with water containing a 0.2% (v/v) spreading agent (containing 80% polyoxyethylene dodecyl ether) and sprayed to the foliage of the test plants at a spray volume of 500 liters per hectare by the aid of a small hand sprayer. Twenty-eight days thereafter, the growth control percentage was observed. The results are shown in Tables 1, 2 and 3 wherein the growth control percentage (%) was determined by weighing the aerial parts of the test plants (fresh weight) and making calculation according to the following equation:

$$\text{Growth controlling percentage (\%)} = \left\{1 - \frac{\text{Fresh weight of test plant in treated plot}}{\text{Fresh weight of test plant in untreated plot}}\right\} \times 100$$

At the time of treatment, catchweed bedstraw, bluestem colorado and stichwort water were about 50 to 80 cm, 50 to 70 cm and 50 to 60 cm in height, respectively.

TABLE 1

Growth controlling percentage against catchweed bedstraw

| | | \multicolumn{5}{c}{Compound (I) (g/ha)} | | | | |
|---|---|---|---|---|---|---|
| | | 0 | 5 | 10 | 20 | 40 | 80 |
| Glufosinate | 0 | 0 | 20 | 42 | 68 | 87 | 99 |
| (g/ha) | 125 | 27 | 64 | 71 | 85 | 99 | 100 |
| | 250 | 49 | 78 | 86 | 99 | 100 | 100 |
| | 500 | 70 | 85 | 98 | 100 | 100 | 100 |
| | 1000 | 89 | 95 | 100 | 100 | 100 | 100 |
| | 2000 | 100 | 100 | 100 | 100 | 100 | 100 |

TABLE 2

Growth controlling percentage against bluestem colorado

| | | \multicolumn{5}{c}{Compound (I) (g/ha)} | | | | |
|---|---|---|---|---|---|---|
| | | 0 | 30 | 60 | 150 | 300 | 600 |
| Glufosinate | 0 | 0 | 25 | 36 | 53 | 75 | 90 |
| (g/ha) | 50 | 25 | 63 | 72 | 84 | 90 | 96 |
| | 100 | 44 | 80 | 89 | 93 | 99 | 100 |
| | 250 | 65 | 92 | 98 | 100 | 100 | 100 |
| | 500 | 83 | 98 | 100 | 100 | 100 | 100 |
| | 1000 | 93 | 100 | 100 | 100 | 100 | 100 |

TABLE 3

Growth controling percentage against stichwort water

| | | \multicolumn{5}{c}{Compound (I) (g/ha)} | | | | |
|---|---|---|---|---|---|---|
| | | 0 | 5 | 10 | 20 | 40 | 80 |
| Bialaphos | 0 | 0 | 22 | 39 | 65 | 82 | 95 |
| (g/ha) | 50 | 16 | 60 | 76 | 89 | 95 | 100 |
| | 100 | 33 | 73 | 90 | 96 | 100 | 100 |
| | 200 | 60 | 88 | 99 | 100 | 100 | 100 |
| | 400 | 77 | 93 | 100 | 100 | 100 | 100 |
| | 800 | 91 | 100 | 100 | 100 | 100 | 100 |

The results in Test Example 1 were analyzed according to the isobole (i.e. equivalent efficacy line) method [Vol. 3, Herbicides, pages 109–111 (1981) in "Noyaku Jikkenho" (Methods in Pesticide Science) edited by Junichi Fukami et al., Soft Science Inc., Tokyo) based on the Tammes's method [Tammes, P.M.L.: Neth. J. Plant Path., 70, 73–80 (1964)]. Namely, several combinations of the compositions having different mixing ratios of Compound (I) and bialaphos or glufosinate but exerting the same level of growth control effect, for example, 90% growth control, were plotted in a graph so as to readily determine a synergistic effect, an arithmetic effect or a competitive effect. In case of exhibiting the synergistic effect, the equivalent efficacy line as plotted is shown below the arithmetic efficacy line.

Figure 2:
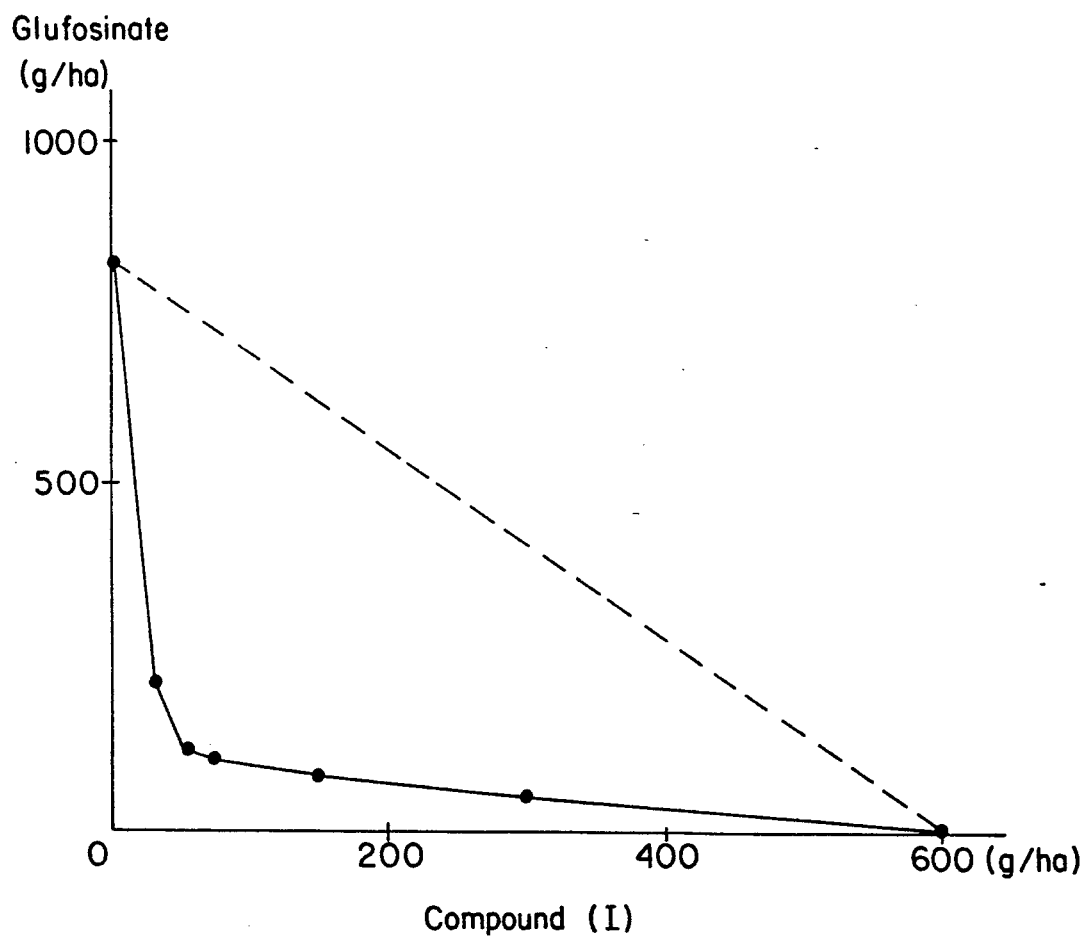
Figure 3:
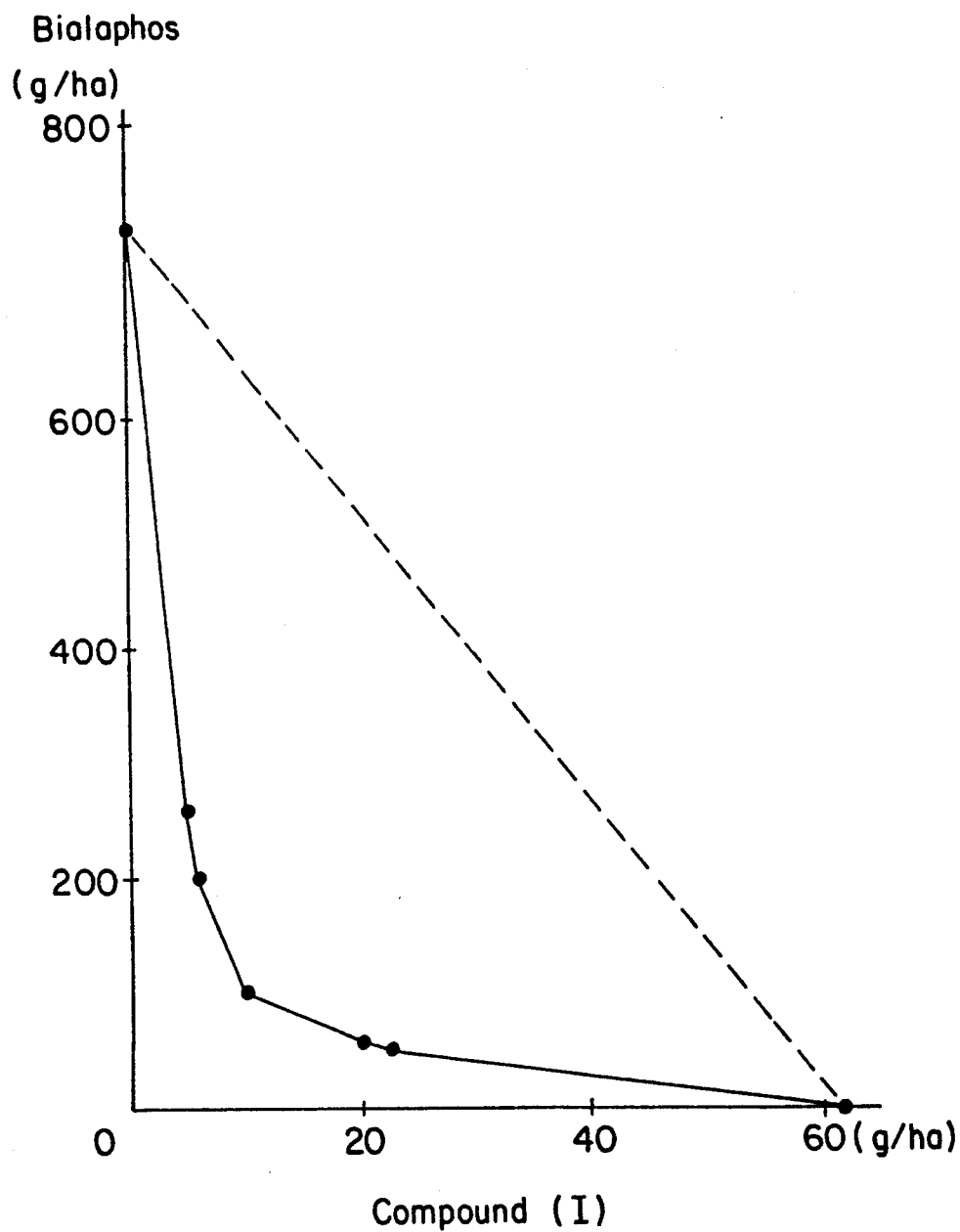

Explaining further in detail with reference to the accompanying drawings, FIG. 1 wherein the ordinate indicates the dosage of glufosinate and the abscissa indicates the dosage of Compound (I), the equivalent efficacy line (i.e. solid line) of 90% growth control of catchweed bedstraw is located under the arithmetic efficacy line (i.e. dotted line); FIG. 2 wherein the ordinate indicates the dosage of glufosinate and the abscissa indicates the dosage of Compound (I), the equivalent efficacy line (i.e. solid line) of 90% growth control of bluestem colorado is located under the arithmetic efficacy line (i.e. dotted line); and FIG. 3 wherein the ordinate indicates the dosage of bialaphos and the abscissa indicates the dosage of Compound (I), the equivalent efficacy line (i.e. solid line) of 90% growth control of stichwort water is located under the arithmetic efficacy line (i.e. dotted line), from which it is understood that the associated use of Compound (I) and glufosinate or bialaphos in a certain mixing ratio produces the synergistic effect.

TEST EXAMPLE 2

Non-cropping lands were plotted into 2 m² per plot, where persian speedwell of 30 to 40 cm in height and other weeds (e.g. common vetch, catchweed bedstraw, stichwort water, japanese hedgeparsley, tall goldenrod, bluestem colorado) of about 60 to 80 cm in satute had grown. A designed amount of the composition in the form of a wettable powder formulated according to Formulation Example 1, 4, 5 or 6 was diluted with water containing a 0.2% (v/v) spreading agent (containing dialkylsulfosuccinate) and sprayed to the foliage of the test plants at a spray volume of 500 liters per hectare by the aid of a small hand sprayer. Twenty-eight days thereafter, the growth control percentage was observed. The results in three replicates are shown in Table 4 wherein the growth control percentage was evaluated according to the same manner as in Test Example 1.

TABLE 4

| | | \multicolumn{7}{c}{Growth control percentage (%)} | | | | | | | |
|---|---|---|---|---|---|---|---|---|
| Test Compound | Dosage (g/ha) | Common vetch | Catchweed bedstraw | Stichwort water | Japanese hedge-parsley | Persian speed-well | Tall golden-rod | Bluestem colorado |
| Compound (I) | 30 | 77 | 80 | 70 | 77 | 93 | 40 | 27 |
| | 330 | 100 | 100 | 100 | 97 | 100 | 83 | 80 |
| Bialaphos | 300 | 90 | 67 | 60 | 83 | 80 | 30 | 57 |
| | 600 | 100 | 80 | 80 | 93 | 93 | 50 | 83 |
| Glufosinate | 300 | 97 | 63 | 60 | 87 | 83 | 40 | 67 |
| | 600 | 100 | 80 | 77 | 93 | 93 | 50 | 87 |
| Compound (I) + Bialaphos | 30 + 300 | 100 | 100 | 100 | 100 | 100 | 90 | 90 |
| Compound (I) + | 30 + | 100 | 100 | 100 | 100 | 100 | 90 | 93 |

TABLE 4-continued

| Test Compound | Dosage (g/ha) | Growth control percentage (%) | | | | | | |
|---|---|---|---|---|---|---|---|---|
| | | Common vetch | Catchweed bedstraw | Stichwort water | Japanese hedge-parsley | Persian speed-well | Tall golden-rod | Bluestem colorado |
| Glufosinate | 300 | | | | | | | |

TEST EXAMPLE 3

Upland fields soil were filled in Wagner pots (200 cm²), and seeds of barnyardgrass were sowed therein and cultivated in a greenhouse until they grew to 40 to 50 cm in statute. A designed amount of the composition in the form of a wettable powder formulated according to Formulation Example 1, 4, 5 or 6 was diluted with water containing a 0.1% (v/v) spreading agent (containing 20% polyoxyethylene glycol alkylphenol ether and 12% ligninsulfonate) and sprayed to the foliage of the test plants at a spray volume of 500 liters per hectare by the aid of a small hand sprayer, and the weeds were separated into two groups. After 3 hours from the spraying, the weeds in one of the groups were drenched with artificial rain (20 mm) over a period of 30 minutes. The weeds in both groups were further cultivated in the greenhouse for 20 days, and the herbicidal activity was observed and rated on 11 indices ranging from 0 (no herbicidal activity) to 10 (complete extermination). The results are shown in Table 5.

TABLE 5

| Test Compound | Dosage (g/ha) | Herbicidal activity | |
|---|---|---|---|
| | | Non-drenched barnyardgrass | Drenched barnyardgrass |
| Compound (I) | 60 | 4 | 2 |
| Glufosinate | 600 | 8 | 4 |
| Bialaphos | 600 | 7 | 4 |
| Compound (I) + Bialaphos | 60 + 600 | 10 | 10 |
| Compound (I) + Glufosinate | 60 + 600 | 10 | 10 |

It is understood from the above results that the composition comprising Compound (I) and bialaphos or glufosinate did not produce any deteriorated herbicidal activity by drenching 3 hours after its application and could completely exterminate barnyardgrass, whereas the herbicidal activity in the sole use of Compound (I), bialaphos or gluphosinate decreased due to rainfall.

What is claimed is:

1. A herbicidal composition which comprises a herbicidally effective amount of the combinations of (a) 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione and (b) one of (2-amino-4-methylphosphinobutyryl)-alanylalanine and its salt or DL-homoalanin-4-yl(methyl)-phosphinic acid and its salt, and an inert carrier or diluent, wherein the weight proportion of the components (a) and (b) is from 1:0.33 to 1:34.

2. The composition according to claim 1, wherein the weight proportion of the components (a) and (b) is from 1:0.5 to 1:34.

3. The composition according to claim 1, wherein the weight proportion of the components (a) and (b) is from 1:1 to 1:34.

4. The composition according to claim 1, wherein component (b) is (2-amino-4-methylphosphinobutyryl-)alanylalanine or its salt.

5. The composition according to claim 1, wherein the component (b) is DL-homoalanin-4-yl(methyl)phosphinic acid or its salt.

6. The composition according to claim 4, wherein the weight proportion of the components (a) and (b) is from 1:0.5 to 1:34.

7. The composition according to claim 4, wherein the weight proportion of the components (a) and (b) is from 1:1 to 1:34.

8. The composition according to claim 5, wherein the weight proportion of the components (a) and (b) is from 1:0.5 to 1:34.

9. The composition according to claim 5, wherein the weight proportion of the components (a) and (b) is from 1:1 to 1:34.

10. A method for controlling weeds which comprises applying a herbicidally effective amount of the composition according to claim 1 to weeds.

11. The method according to claim 10, wherein the total amount of the components (a) and (b) is from 100 to 2000 grams per hectare.

12. The method according to claim 10, wherein the total amount of the components (a) and (b) is from 150 to 2000 grams per hectare.

13. The method according to claim 10, wherein the weeds are those germinated in the non-agricultural fields or non-cropping lands.

14. The method according to claim 10, wherein the total amount of the components (a) and (b) is from 200 to 2000 grams per hectare.

15. The method according to claim 10, wherein the component (b) in the composition is (2-amino-4-methylphosphinobutyryl)alanylalanine or its salt.

16. The method according to claim 10, wherein the component (b) in the composition is DL-homoalanin-4-yl-(methyl)phosphinic acid or its salt.

17. The method according to claim 15, wherein the weight proportion of the components (a) and (b) in he composition is from 1:0.5 to 1:34.

18. The method according to claim 16, wherein the weight proportion of the components (a) and (b) in the composition is from 1:0.5 to 1:34.

* * * * *